United States Patent [19]
Marshall et al.
[11] Patent Number: 4,469,092
[45] Date of Patent: Sep. 4, 1984

[54] SCALP STIMULATING SYSTEM

[76] Inventors: Walter D. Marshall; James W. Garrison, Jr., both of 20515 Aldine - Westfield #77, Humble, Tex. 77338

[21] Appl. No.: 424,070
[22] Filed: Sep. 27, 1982
[51] Int. Cl.[3] ..................... A61M 1/00
[52] U.S. Cl. ..................... 128/36; 128/49; 128/62 R; 604/315
[58] Field of Search ..................... 128/24.2, 24 R, 34, 128/32, 35-37, 48, 49, 52, 62 R, 64, 44, 45; 604/74, 313, 315

[56] References Cited

U.S. PATENT DOCUMENTS

| | | | |
|---|---|---|---|
| 1,355,679 | 10/1920 | McConnell | 128/24 R |
| 2,232,254 | 2/1941 | Morgan | 128/45 |
| 2,338,339 | 1/1944 | La Mere et al. | 128/64 |
| 2,427,610 | 9/1947 | Konig | 128/62 R |
| 3,481,326 | 12/1969 | Schamblin | 128/24.2 |
| 3,716,048 | 2/1973 | Alonso | 128/49 |
| 3,763,853 | 10/1973 | Jochimski | 128/36 |

*Primary Examiner*—Richard J. Apley
*Assistant Examiner*—Harry J. Macey
*Attorney, Agent, or Firm*—Stephen D. Carver

[57] ABSTRACT

An electro mechanical system for stimulating the human scalp. The system includes a rigid helmet adapted to be placed upon the head of a patient to be treated, which helmet includes an internal pad comprising integral, stimulating finger members which directly contact the scalp of the patient. A vibration motor housed within the helmet communicates mechanically with the pad to gently vibrate same to stimulate the scalp. Remote means for generating a vacuum are interconnected with the helmet through an elongated vacuum hose, and a vacuum input orifice is defined within the helmet. Preferably the vibration motor is housed within the vacuum inlet orifice, and vacuum is distributed interiorly of the helmet during vibration to stimulate the scalp.

5 Claims, 8 Drawing Figures

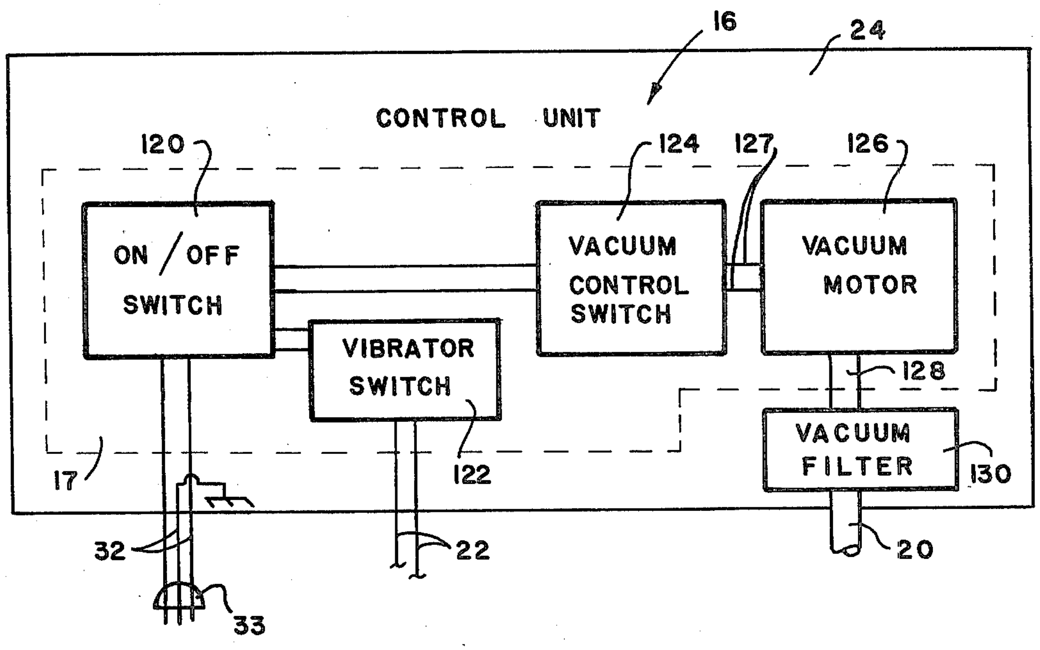
FIG. 8
FIG. 7
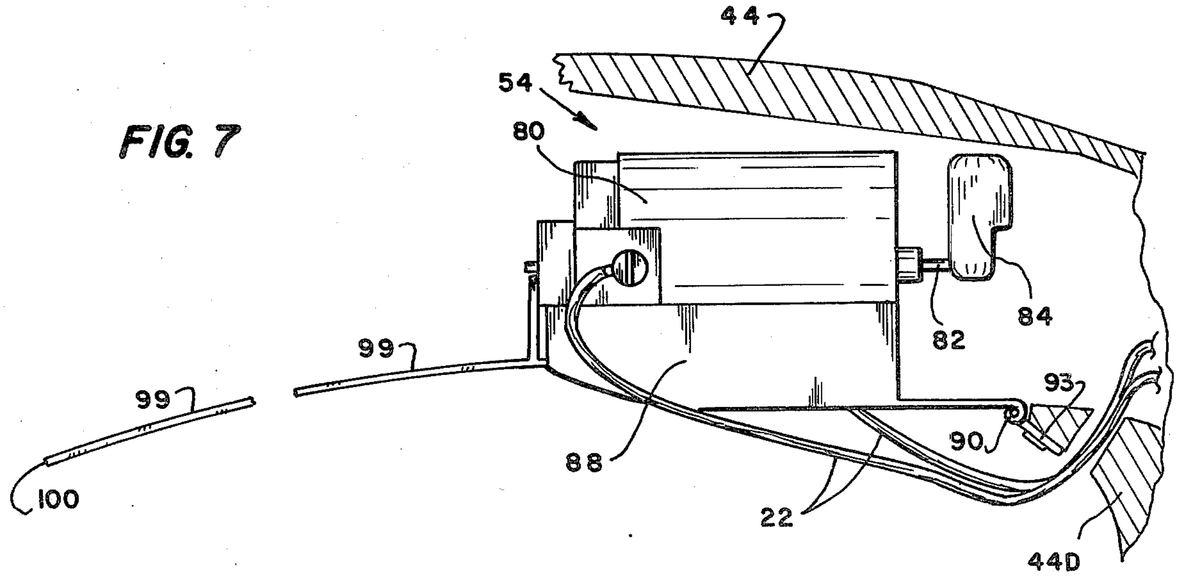

SCALP STIMULATING SYSTEM

BACKGROUND OF THE INVENTION

This invention relates to scalp massage devices. More particularly, the present invention is concerned with a scalp massage unit in which vacuum suction and vibration are transmitted directly to the scalp of the patient to stimulate the scalp and provide a gentle massaging effect.

A plurality of inventors have previously recognized the desireability of stimulating the human scalp. A variety of different electro-mechanical devices have been proposed in the prior art. As will be appreciated by those skilled in the art, regular washing and massaging of the human scalp promotes health and cleanliness. Most of the prior art devices include some form of movable or vibrating fingers which in effect massage the scalp to promote health.

For example, U.S. Pat. No. 3,763,853 issued Oct. 9, 1973 discloses a head vibrator including a plurality of massaging fingers projecting inwardly from a housing to contact the human skull. A vibrating system is employed to gently massage the skull by manipulating mechanical fingers. U.S. Pat. Nos. 2,427,610 and 849,844 both depict vibrating devices which, when suitably placed relative to the skull of the patient, stimulate the scalp by direct physical contact by a variety of moving fingers or "applicators". Other relatively similar devices are shown in U.S. Pat. Nos. 2,914,065 and 2,232,254. U.S. Pat. No. 2,706,980 discloses a scalp massage implement which fingers are operated independently in separate groups. U.S. Pat. No. 1,861,924 discloses a vacuum operated head in which vibration is produced by air forced through a turbine system. The turbine includes eccentric weights for producing vibration. The latter device employs vibration in conjunction with suction to dislodge dirt particles for more effective vacuuming.

Our research and experiments indicate that the human scalp may effectively be mechanically massaged by combining rapid vibration distributed over a wide area of the scalp with concurrent suction.

SUMMARY OF THE INVENTION

The present invention comprises an electro-mechanical system for stimulating the human scalp.

The invention includes a rigid, generally hemispherical helmet adapted to be worn by the user. The helmet includes a rigid, preferably plastic outer shell which houses an inner vibration pad preferably made of plastic, rubber or the like. The pad includes a plurality of integral downwardly projecting, spaced-apart fingers which directly contact the scalp. Vibration means are provided within the helmet to mechanically vibrate the pad fingers. Preferably an unbalanced motor is employed to generate vibration, and preferably the motor is coupled to the pad through a plurality of radially outwardly extending, arcuate spaced-apart fingers which terminate in a rigid, generally arcuate termination radius.

Vacuum is supplied to the helmet by an elongated hose which runs to a conventional vacuum source. The hose is coupled to the helmet and air is drawn upwardly through suction through the helmet through an air orifice. Preferably the vibration motor is physically positioned within the latter orifice. A plurality of vents defined in the vibration pad distribute air flow. Preferably the lower inner periphery of the helmet is provided with a removable cushion which allows the helmet to be gently and comfortably worn by the user.

Moreover, this removable cushion tends to create a vacuum seal about the head of the wearer, to promote the effects of suction upon the human scalp.

Thus an object of the present invention is to provide an electro-mechanical system for stimulating the human scalp.

More particularly, a primary object of the present invention is to promote the growth of hair upon the human scalp.

Yet another object of the present invention is to combine vacuum with mechanical vibration to produce a stimulating and healthy effect upon the human scalp.

Yet another object of the present invention is to provide a system of the character described in which vibration is uniformly distributed about the scalp of the user.

Yet another object of the present invention is to provide an electro-mechanical system for stimulating hair growth in human users, which system may be transported easily about by the user.

These and other objects and advantages of the present invention, along with features of novelty appurtenant thereto, will appear or become apparent in the course of the following descriptive sections.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views;

FIG. 7 is an enlarged view of the motor vibration system; and,

FIG. 8 is an electrical block diagram of the control unit preferably employed in conjunction with the remote helmet assembly.

DETAILED DESCRIPTION OF THE DRAWINGS

Figure 1:
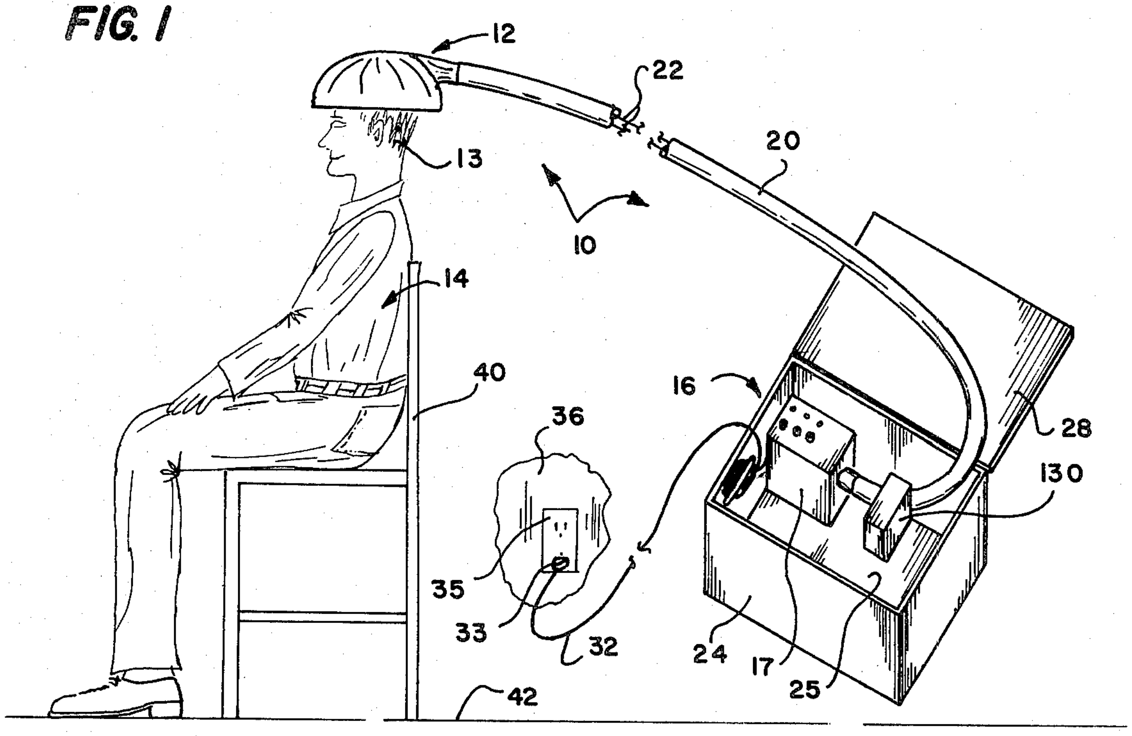
FIG. 1 is a fragmentary, pictorial view illustrating use of the present invention upon a typical user.
Figure 2:
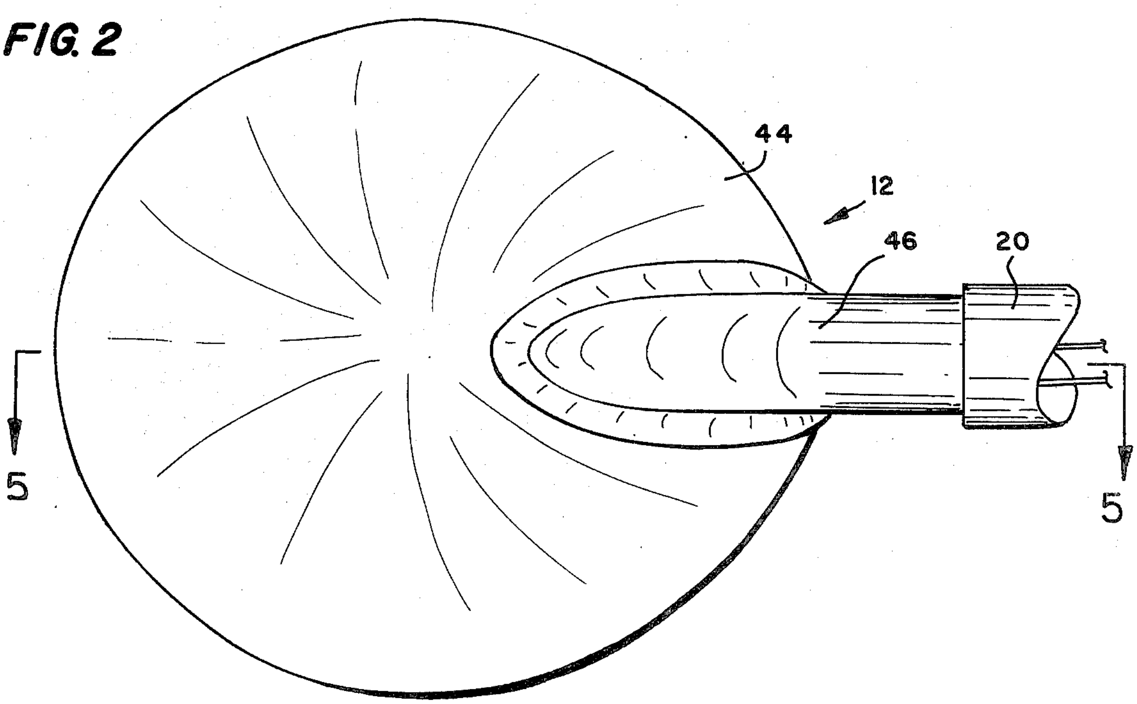
FIG. 2 is an enlarged, fragmentary top plan view of the preferred helmet contemplated by the present invention.
Figure 3:
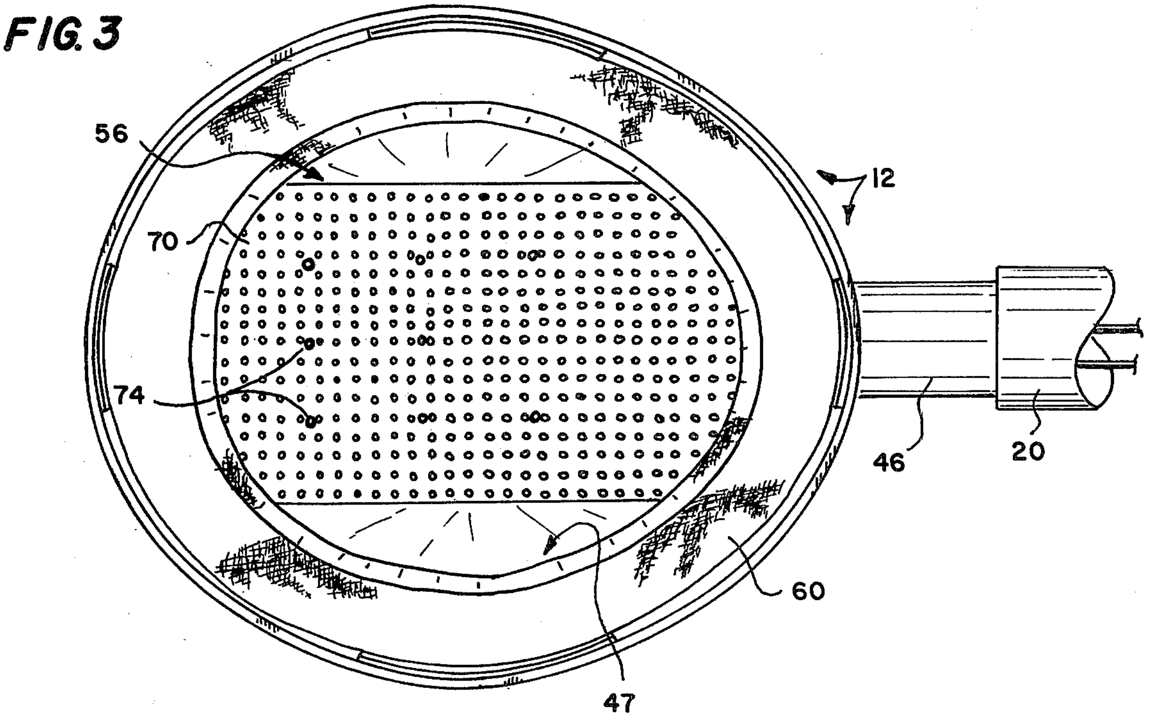
FIG. 3 is a fragmentary, bottom plan view of the preferred helmet, with the peripheral cushion means installed.
Figure 4:
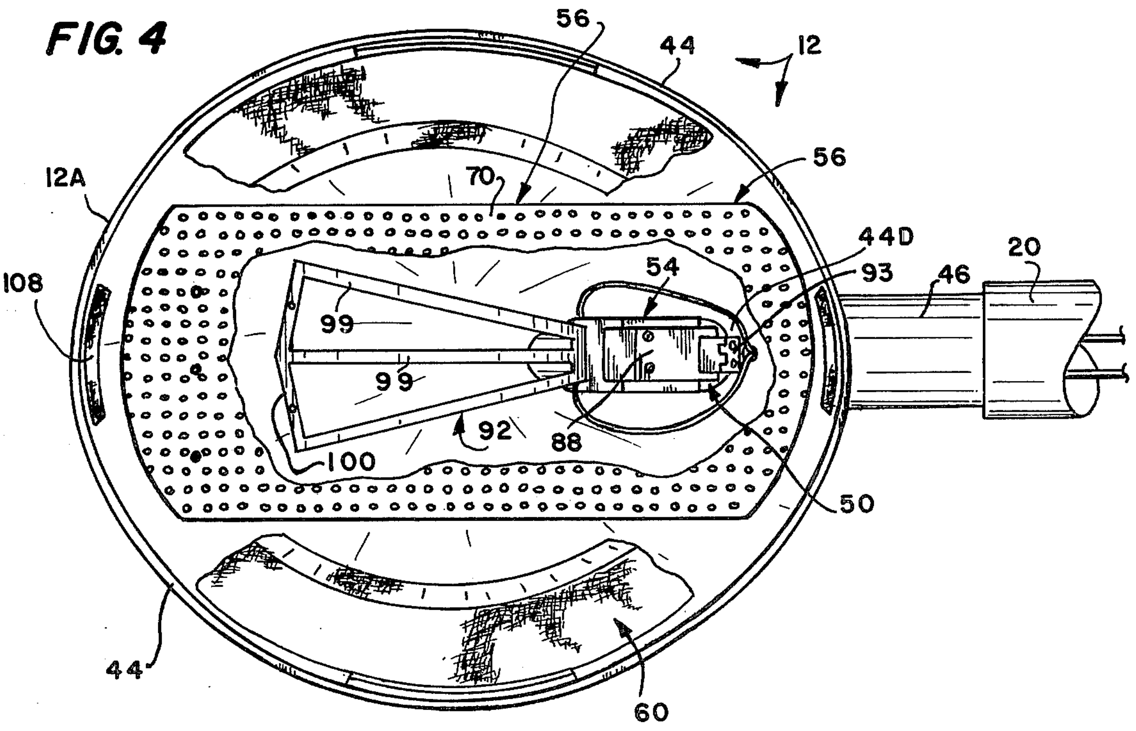
FIG. 4 is a fragmentary bottom plan view of the helmet similar to FIG. 3, in which major portions have been broken away for purposes of clarity.
Figure 5:
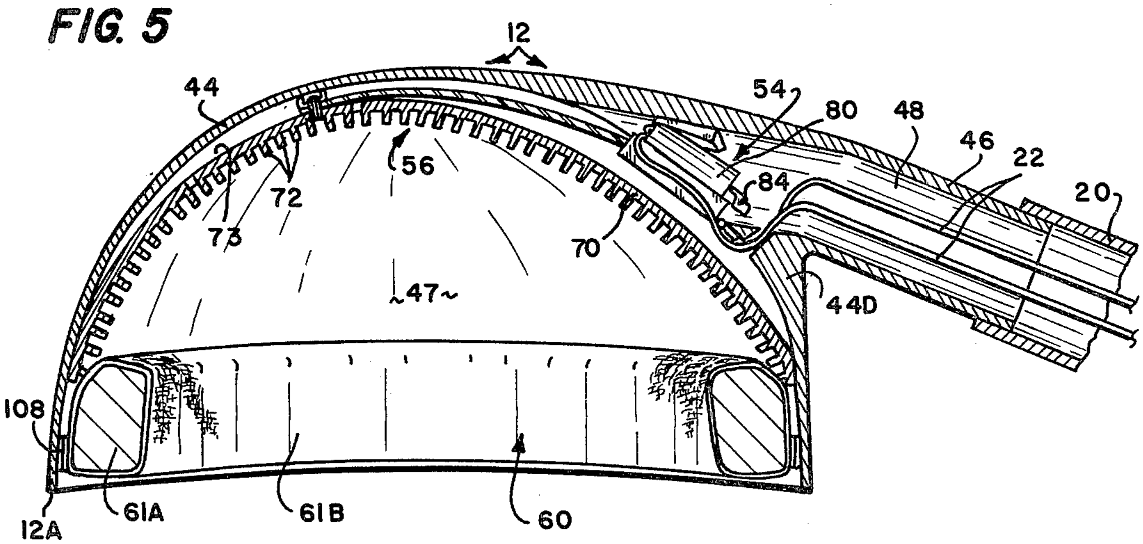
FIG. 5 is a longitudinal sectional view of the helmet taken generally along lines 5—5 of FIG 2.
Figure 6:
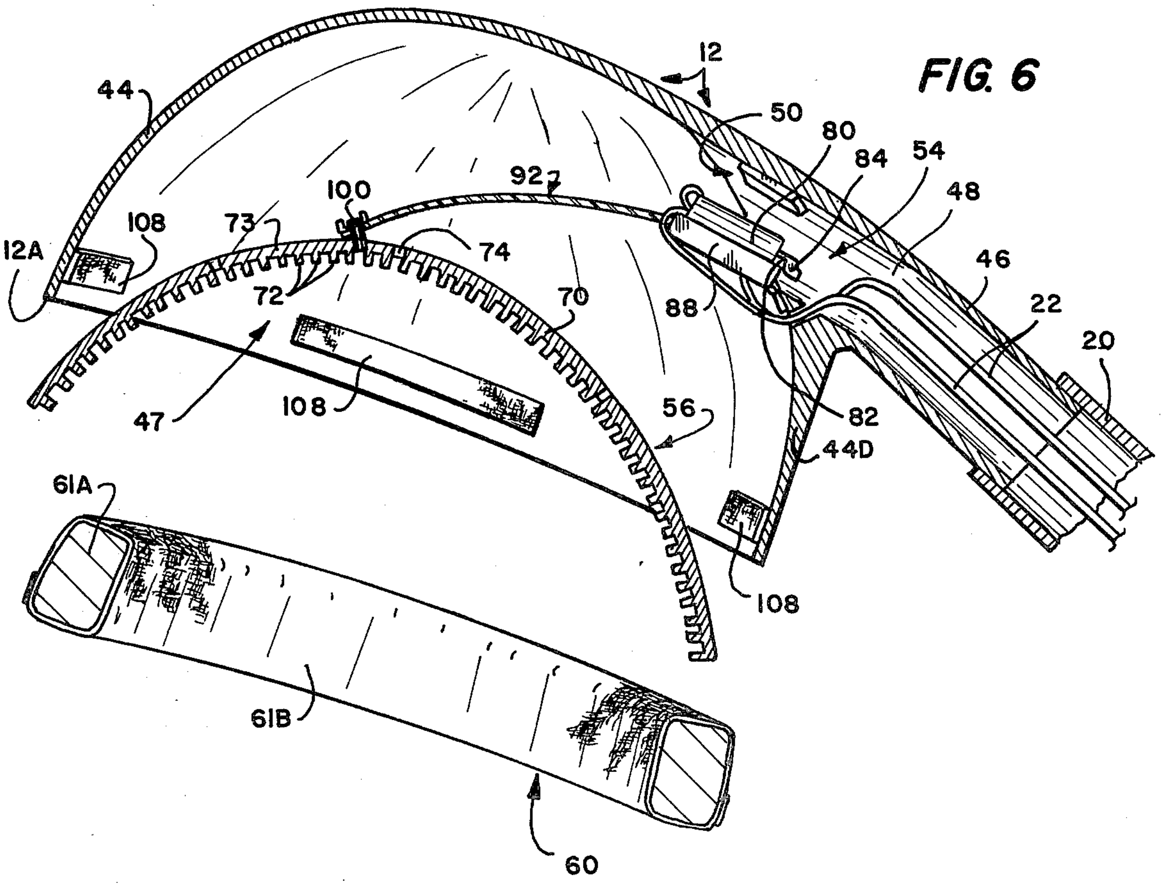
FIG. 6 is an exploded, fragmentary sectional view of the helmet means.

With initial reference now to FIG. 1 of the appended drawings, a system for stimulating the human scalp has been generally designated by the reference numeral 10. System 10 includes a unique helmet system 12 adapted to be worn upon the head 13 of a patient 14. Helmet 12 is interconnected with a remote control unit, generally designated by the reference numeral 16 through a conventional, elongated hose 20 in which a pair of electrical conductors 22 are preferably disposed. Preferably the control unit 16 is housed within a suitable, portable, generally cubical mechanical enclosure 24 including an interior 25 adapted to store hose 20 and helmet 12, and including a top 28 hingably coupled to the enclosure for sealing the interior 25. Electrical apparatus is disposed within metallic chassis 17.

Control unit 16 is powered through a conventional electrical cable 32 terminating in a conventional plug 33 received within wall socket 35. Patient 14 ideally should sit within a comfortable chair 40, appropriately disposed upon floor 42, adjacent to wall 36, or spaced apart therefrom within convenient range of hose 20.

With reference now to FIGS. 2–7, the helmet assembly 12 is preferably formed of plastic, and it is of rigid, generally hemispherical shape. Helmet 12 comprises a rigid, outer shell 44 adapted to conform generally to the geometry of the patients head 13. As best viewed in FIG. 2, hose 20 terminates in a rigid pipe-like member 46 extending from shell 44 and integral therewith. Shell 44 delivers vacuum from pipe 20 to the interior 47 of the helmet 12 through its own internal passageway 48 and a vacuum addmission orifice 50 in fluid flow communication with passageway 48. The shell 44 houses vibration generation means, generally designated by the reference numeral 54, a separate massage pad system, generally designated by the reference numeral 56, and a removable, peripheral cushion 60 disposed about the inner, radial periphery of the bottom 12A of helmet 12.

The pad system 56 comprises a resilient sheet 70 from which a plurality of individual stimulating fingers 72 project. As appreciated from an inspection of FIGS. 5 and 6, these fingers 72 project toward the interior 47 of the helmet 12. Thus, head 13 of the patient 14 will be directly contacted by them. Sheet 70 is dimensioned to properly fit within the upper confines of the interior 47 of shell 44, and, as viewed in FIG. 5 and 6, it is of generally curved cross section, conforming generally to the interior geometry of the helmet shell 44. Also, a plurality of spaced apart venting orifices 74 are defined within section 70 of the pad 56 to facilitate distribution of air currents and flow.

As best viewed in FIG. 7, the vibration means 54 comprises a conventional electric motor 80 powered by conventional electric lines 22. Motor 80 includes an output shaft 82 secured to an unbalanced weight 84 which, in response to rotation, generates severe vibration. Motor 80 is secured to rigid, generally rectangular mount 88 which includes a hinge assembly 90 to pivotally secure the motor assembly to the rear region 44D of the helmet with a pair of conventional screws 93. Motor 80 is powered by lines 22, and, in response to actuation, severe vibration will be experienced by housing 88.

A plurality of spaced apart, rigid vibration transmitting fingers, generally designated by the reference numeral 92, extend from housing 88 into physical contact with the top surface 73 of the pad assembly 56. In particular, these vibration distributing fingers 92 include individual curved, elongated members 99 which extend from housing 88 and terminate in an elongated, generally arcuate termination radius 100 fixed to the top 73 of the pad means 70. When the individual vibration fingers 99 terminate in the arcuate termination 100 along the lines discussed, we have found the effects of the apparatus to be maximized.

The removable cushion 60 is adapted to be secured to the lower inner radial periphery of the helmet 44. As best viewed in FIG. 3, cushion 60 is of generally eliptical geometry, and it is formed of suitable cushion material such as foam rubber or the like. It is removably secured within the inner periphery of the helmet by a plurality of cooperating Velcro-brand fastener strips, generally designated by the reference numeral 108. Suitable Velcro-brand fastening devices are fastened both to the cushion 60 and to the inner radial periphery of the lower confines of the helmet in suitable spaced apart intervals to retain cushion 60 in desired orientation. Preferably cushion 60 includes a foam rubber interior 61A surrounded by a suitable enviromentally protective enclosure 61B perferably made of plastic or the like.

With reference now to FIG. 8, oepration of control unit 16 is faciliated by supplying nominally 120 volts alternating current power via plug 33 and line 32 to a control switch 120. When switch 120 is activated, a separate vibrator switch 122 may transmit electric current along lines 22 to motor 80 to produce vibrations as discussed previously. Vacuum control switch 124, also controlled by master switch 120, activates a conventional vacuum motor 126 via lines 127. This conventional motor is coupled to a conventional vacuum filter 130 via conventional hose 128. Filter 130 is coupled to the terminal end of vacuum hose 20. Thus, by properly actuating switch 120, 122 and/or 124, a combination of vacuum and/or mechanical vibration stimulation may be generated with the use of helmet 12. Our experiments have revealed that scalp stimulation and massaging is greatly facilitated with use of this device.

From the foregoing, it will be seen that this invention is one well adapted to obtain all the ends and objects herein set forth, together with other advantages which are obvious and which are inherent to the structure.

It will be understood that certain features and subcombinations are of utility and may be employed without reference to other features and subcombinations. This is contemplated by and is within the scope of the claims.

As may possible embodiments may be made of the invention without departing from the scope thereof, it is to be understood that all matter herein set forth or shown in the accompanying drawings is to be interpreted as illustrative and not in a limiting sense

What is claimed is:

1. A system for massaging and treating the human scalp, said system comprising:
   - helmet means adapted to be placed upon the head of a patient to be treated, said helmet means comprising:
     - a rigid, substantially hollow shell means greater in size than the head of the patient;
     - separate pad means disposed within said shell means and including a plurality of resilient, spaced apart integral finger members adapted to directly contact the scalp of the patient;
     - vibration means disposed within said helmet means between said shell means and said pad means for vibrating said pad means to massage the patients scalp, said vibration means comprising:
       - vibration generating motor means; and,
       - a plurality of spaced apart vibration transmitting fingers projecting from said vibration motor means in to physical contact with said vibration pad means;
   - means for supplying vacuum to said shall means; and,
   - control means for actuating said vacuum means and said vibration generating motor means.

2. The combination as defined in claim 1 wherein:
   said vacuum means comprises an elongated hose communicating internally of said shell means through a vacuum input orifice defined in said shell means; and, said vibration means motor means is secured to said helmet means interiorly of said shell means and operatively positioned within said vacuum orifice.

3. The combination as defined in claim 2 wherein said pad means includes a plurality of vent holes for exposing the scalp of a patient to suction during vibration.

4. The combination as defined in claim 3 wherein said vibration transmitting fingers terminate at a fixed, rigid, arcuate termination radius affixed to said pad means in spaced relation relative to said vibration motor means.

5. The combination as defined in claim 4 including peripheral cushion means removably attached to the, inner periphery of said shell means for aiding the wearing of said helmet means by contacting the lower portion of the patients head, and for helping provide a vacuum seal.

* * * * *